(12) United States Patent
Ritzberger et al.

(10) Patent No.: US 7,795,164 B2
(45) Date of Patent: Sep. 14, 2010

(54) DENTAL GLASS

(75) Inventors: Christian Ritzberger, Nenzing (AT); Volker Rheinberger, Vaduz (LI); Elke Apel, Sevelen (CH); Peter Burtscher, Rankweil (AT); Wolfram Höland, Schaan (LI); Thomas Graule, Schaffhausen (CH); Simone Zürcher, Bellinzona (CH); Andri Vital, Zürich (CH)

(73) Assignees: Ivoclar Vivadent AG, Schaan (LI); Empa Dubendorf, Dubendorf (CH)

( * ) Notice: Subject to any disclaimer, the term of this patent is extended or adjusted under 35 U.S.C. 154(b) by 306 days.

(21) Appl. No.: 12/083,821

(22) PCT Filed: Sep. 25, 2006

(86) PCT No.: PCT/EP2006/066702

§ 371 (c)(1),
(2), (4) Date: May 12, 2008

(87) PCT Pub. No.: WO2007/048670

PCT Pub. Date: May 3, 2007

(65) Prior Publication Data

US 2009/0113936 A1    May 7, 2009

(30) Foreign Application Priority Data

Oct. 27, 2005   (DE) ........................ 10 2005 051 387

(51) Int. Cl.
*C03C 3/095*    (2006.01)
*A61K 6/06*    (2006.01)

(52) U.S. Cl. ........................... 501/64; 106/35; 523/117; 65/21.1; 65/21.2

(58) Field of Classification Search .................. 501/64; 106/35; 65/21.1, 21.2; 523/117
See application file for complete search history.

(56) References Cited

U.S. PATENT DOCUMENTS

| 6,121,344 | A  |   | 9/2000 | Angeletakis et al. |        |
|-----------|----|---|--------|--------------------|--------|
| 6,297,181 | B1 | * | 10/2001| Kunert et al. ...............| 501/57 |
| 7,098,259 | B2 | * | 8/2006 | Hoescheler et al. .........| 523/117|
| 7,687,418 | B2 | * | 3/2010 | Peuchert et al. ............| 501/64 |
| 2007/0184964 | A1 | * | 8/2007 | Peuchert et al. ..........| 501/32 |

FOREIGN PATENT DOCUMENTS

| DE | 34 21 155  | 12/1985 |
| DE | 43 23 143  | 12/1994 |
| DE | 197 13 048 | 10/1998 |
| DE | 102005051387 | 1/2007 |

* cited by examiner

*Primary Examiner*—Karl E Group
(74) *Attorney, Agent, or Firm*—Lucas & Mercanti, LLP; Klaus P. Stoffel

(57) ABSTRACT

The present invention relates to a dental glass containing 50 to 70 wt. % of $SiO_2$,
5 to 18 wt. % of $Al_2O_3$,
6.1 to 30 wt. % of MgO,
1 to 15 wt. % of $La_2O_3$,
1 to 15 wt. % of $WO_3$,
0.1 to 8 wt. % of $ZrO_2$,
and optionally further oxides except for the oxides of Sr, Ba or alkali metals, wherein the stated quantities in total add up to 100 wt. %.

19 Claims, No Drawings

DENTAL GLASS

This application claims the priority of DE 10 2005 051 387.5-45.

The present invention relates to a dental glass, a method for the production thereof and the use thereof.

The dental glasses used today are mainly low-melting glasses with a low refractive index of n=1.50 to 1.53 matched to the monomer or monomer mixture. However, the previously used dental glasses with this low refractive index have the disadvantage of low chemical stability, which manifests itself in etching or even degradation of the filler components in the composite.

A widely used dental glass system is described in DE 43 23 143 C1. This system, $SiO_2$—BaO/SrO—$B_2O_3$—$Al_2O_3$, has a high SrO content. A similar system, which contains BaO, is known from U.S. Pat. No. 6,121,344.

Furthermore, alkali metal oxide-containing glasses and the use thereof as dental fillers are known from DE 198 49 388 A1. A disadvantage in this system is that the alkali metal ions and the fluorine decrease the chemical stability of the glass.

In the state of the art, $WO_3$ and $La_2O_3$-containing glasses are used for example in the high performance optics field (Glaschemie, pp. 444ff, Vogel et al., Springer Verlag 1992). However, these glasses have a high refractive index. Furthermore, they have very low $SiO_2$ and phosphate contents. In view of the refractive index of these systems, such glasses are unsuitable for dental applications.

Furthermore, from DE 34 21 155 A1, dental glasses are known which are used as filler components. However, as well as $WO_3$ and $La_2O_3$, the compositions described there contain very high contents of SrO. Furthermore, the refractive index of this glass is 1.55 and above. On account of this high refractive index and the other stated disadvantages, this glass is less suitable for use as a dental composite.

Finally, from U.S. Pat. No. 6,121,344, a barium silicate glass is known which is produced by a special milling process. In this milling process, a mean particle size of 500 nm (=0.5 μm) is obtained. Since in recent years an increasing tendency to dispense with the use of BaO in dental glasses because of possible toxic effects has been observed, these glasses are little used as fillers for use in dental technology.

The object of the invention is thus to provide glasses as inorganic fillers for dental composites which no longer have the known disadvantages of the state of the art, and in particular exhibit high opacity to X-rays and a suitable low refractive index. Likewise, the use of barium oxide, strontium oxide and alkali metal oxides is avoided. In addition, the dental composites produced with fillers on the basis of the glasses according to the invention should exhibit very good mechanical properties (strength and elastic modulus), improved abrasion properties and good optical properties. In addition, the refractive index should be optimized. Finally, a suitable opacity to X-rays should be achieved. Further, the glasses should also have good chemical stability towards dilute NaF solutions, since as a result of the action of fluoride on silicate glasses leaching or even complete dissolution of the filler particles from the cured monomer matrix of the composite can occur.

Finally, from DE 197 13 048 A1, dental composites based on normal polymerizable monomers, initiators, fillers and other additives which preferably contain glasionomer cements as slag-inhibiting addition salts of acid-functional polymers with mono- or polyvalent cations. However, from the disclosure of this patent application, no indication emerges as to, for example, the avoidance of SrO and alkalis or the selection of MgO and $WO_3$ from a whole range of components mentioned equally.

The purpose of the invention is achieved by means of dental glasses containing 50 to 70 wt. % of $SiO_2$, 5 to 18 wt. % of $Al_2O_3$, 6.1 to 30 wt % of MgO, 1 to 15 wt. % of $La_2O_3$, 1 to 15 wt. % of $WO_3$ and 0.1 to 8 wt. % of $ZrO_2$.

The sum of $La_2O_3$+$WO_3$ is 8 to 20 wt. % and that of $Al_2O_3$+$La_2O_3$+$WO_3$ preferably 16 to 38 wt. %. The stated wt. % overall add up to 100 wt. %.

In a preferred embodiment, the dental glasses contain 50 to 70 wt. % of $SiO_2$, 9 to 15 wt. % of $Al_2O_3$, 6.1 to 30 wt % of MgO, 1 to 12 wt. % of $WO_3$ and 0.1 to 8 wt. % of $ZrO_3$. The sum for $La_2O_3$+$Y_2O_3$ is preferably 1 to 18 wt. %, and the sum for $La_2O_3$+$Al_2O_3$+$Y_2O_3$+$ZrO_2$ is preferably 16 to 35 wt. %. Here $Y_2O_3$ is preferably used as a partial replacement for $La_2O_3$.

In a preferred embodiment, the dental glasses contain 6.1 to 20 wt. % of MgO, preferably 6.1 to 12 wt. % of MgO.

Further, it is preferable that the dental glasses contain from 0 to 15 wt. % of other divalent metal oxides, apart from Sr and Ba, preferably CaO and ZnO.

Apart from the oxides of divalent metals, oxides of tri- or tetravalent metals can also be contained in the dental glasses. Contents of 0 to 20 wt. % of oxides of trivalent and/or tetravalent metals are preferred.

The preferred oxides here include $B_2O_3$ and $TiO_2$.

According to the invention, it is also advantageous to use $Ag_2O$. Contents of 0 to 4 wt. %, preferably 0.1 to 2.0 wt. % are preferable here.

If necessary, further oxides except for the oxides of Sr, Br and the alkali metals can be contained. Finally, halides and sulfates can also be contained in the dental glasses according to the invention. These are preferably contained in quantities of 0 to 2 wt. %.

The good chemical stability, especially against the action of fluoride, is achieved in that the use of ions which strongly increase the solubility of the glass is avoided. This applies especially to all alkali metal ions. Hence for a stable, poorly soluble silicate network, $Al_2O_3$, $ZrO_2$, $WO_3$, $La_2O_3$ and $Y_2O_3$ are mainly incorporated. The ions of Ca, Mg and Zn enable better fusibility of the glasses and at the same time enable a good and homogeneous glass phase. Furthermore, it was surprisingly found that in spite of the high contents of $WO_3$ and $La_2O_3$ or even MgO, no clouding phenomena could be observed. In such a case, this glass would not be suitable as a filler of dental materials.

Surprisingly, it was possible to develop a magnesium aluminosilicate glass which exhibits high contents of $R(III)_2O_3$ (wherein $R(III)_2O_3$ represents the sum of $La_2O_3$ and $Y_2O_3$), and $WO_3$ and $ZrO_2$ and has a high X-ray opacity and a refractive index of only about 1.50 to 1.549.

Moreover, the compositions according to the invention have the surprising effect that on the one hand a high X-ray opacity and on the other a refractive index of 1.50 to 1.549 are achieved. Apart from this, the dental materials produced with the dental glasses according to the invention have very good chemical stability. Since no BaO and no SrO or alkali metal oxides were used, the dental glass or the filler produced therefrom also does not exhibit the disadvantages known from the state of the art. The said refractive indices of 1.50 to 1.549 were achieved although in particular $La_2O_3$, $Y_2O_3$, $WO_3$ and $ZrO_2$ were used as glass components for increasing the refractive index of glasses.

The usual monomers for dental composites have a refractive index of about 1.47 to 1.53. More refractive monomers require dental glasses appropriately matched as regards refractive index. With the dental glass development according to the invention, refractive indices in the range from 1.50 to 1.549 have now become possible. The dental glasses according to the invention and the dental materials produced from these fillers exhibit good chemical stability towards fluoride solutions, which in particular enter the oral cavity during use of such toothpastes or oral rinse solutions. With conventional dental glasses, leaching or complete dissolution of the filler particles from the cured monomer matrix can occur as a result of the action of fluoride. This process leads to a loss of gloss of the restorative work, increasing roughness and plaque formation and represents an esthetic and also hygiene problem for the patients.

A further advantage of the dental glasses according to the invention is that their X-ray opacity is improved. This is important for the dentist for the detection of excesses, marginal gaps and secondary caries. As already described, this is achieved through the use according to the invention of the oxides of Zr, La, Y and W.

The dental glasses according to the invention are used essentially in powder form for fillers.

A further aspect of the present invention is the method for the production of the dental glasses according to the invention as powder, wherein a melt of a starting glass which contains the oxides described is fused at temperatures from about 1400° C. to about 1700° C., preferably at 1600° C. to 1670° C. and homogenized during a period of 0.5 to 6 hours, preferably 1 to 2 hours, the melt is quenched by fritting (rapid cooling of the melt by pouring into cold water) (avoidance of the phase separation and clouding to which high MgO-content glasses are usually prone) and creation of small glass granules.

The glass granules produced in this manner are then pre-pulverized. This results in pulverization to a mean particle size of 1 to 50 μm, preferably 1 to 20 μm. The pulverization is preferably effected in a jet or ball mill.

The pre-pulverization is followed by fine milling. This effects a pulverization to preferably 0.5 to 5 μm, especially preferably 1 to 2 μm. In a preferred embodiment, wet milling is used. For this, polyurethane or ceramic coated annular gap ball mills are preferably used.

The wet milling is effected using dispersants, preferably deionized water. The solids content is preferably 5 to 50 wt. %, especially preferably between 5 and 35 wt. %.

In a preferred embodiment, yttrium-stabilized $ZrO_2$ grinding balls are used. However, $Al_2O_3$ or even glass grinding balls of the same composition as that according to the invention are also suitable for the fine milling.

According to the invention, it was surprisingly found that with the stated solids contents a two-stage fine grinding is especially advantageous. In this, in a first pulverization step with a solids content of 30 to 40 wt. %, especially preferably ca. 33 wt. % and a subsequent second milling step with a solids content of 5 to 15 wt. %, especially preferably 10 wt. %, the specific surface area of the milling stock is substantially changed. After about 40 minutes' milling time at 30 to 40 wt. % solids content a specific surface area of 50 to 60 $m^2/g$ is first attained, and after a reduction in the solids content to 5 to 15 wt. % and a further 480 minutes' milling time, a specific surface area of 100 to 110 $m^2/g$.

The specific surface area can be determined by BET analysis (Beckman-Coulter, SA 3100). For this, the suspension was dried for 30 mins at 160° C. and degassed for 3 hours under a nitrogen atmosphere. Image analysis of a transmission electron micrograph (Philips CM 30, Royal Philips Electronics, Eindhoven, NL) showed that the particles are less than 50 nm in size.

From the TEM micrographs and the specific surface area, a mean particle size of ca. 20 nm was determined.

The glass powder obtained by the fine milling has a particle size of 10 to 50 nm. Preferably the particle size is ca. 20 to 40 nm.

The dental glasses according to the invention thus produced can be used as glass fillers for dental composites. For this, coupling agents are firstly applied by silanization. Stabilizers and inhibitors are then added. Inorganic fillers (Aerosil), $YF_3$, and dyes/pigments (e.g. iron oxide) are then added. Finally, incorporation into a monomer mixture with a polymerization initiator, e.g. camphorquinone, is effected. In conclusion, the curing then takes place.

Below, the invention is explained in more detail with reference to the examples:

1. Production Of The Dental Glasses

The glasses were fused from pure raw materials as described above at temperatures between 1600 and 1670° C. and homogenized for 1.5 hours.

For production as filler, the glasses were produced as glass frits. This means that the glass melt is rapidly quenched, so that the highly disordered state of the melt is frozen by supercooling (frozen supercooled melt). In this way, it was generally possible with the MgO-containing glasses according to the invention to bypass the phase separation and obtain a transparent glass in powder form.

The pre-pulverization of the glass frit was effected as needed by means of a jet or ball mill to an achieved mean particle size of 5 to 30 μm. The milling to the desired particle fineness ($d_{50}$ of ca. 1.5 μm after 30 minutes or $d_{50}$ of ca. 0.7 μm after 150 minutes) was effected by wet milling in a polyurethane or ceramic-coating annular gap ball mill. Deionized water is used as the dispersant at a solids content of 5 to 50 wt. %. As the grinding balls, yttrium-stabilized $ZrO_2$ grinding balls, $Al_2O_3$ or even glass grinding balls of the same composition were used for auto-pulverization.

After a first pulverization step with a solids content of 33 wt. % and a subsequent second milling step with a solids content of 10 wt. %, the specific surface area of the milling stock was measured. After 480 minutes' milling time at 33 wt. %, a specific surface area of 55.5 $m^2/g$ was attained, and after a reduction in the solids content to 10 wt. % and a further 480 minutes' milling time, a specific surface area of 106.09 $m^2/g$.

The refractive index was measured on glass powder by the Becke method. Cargille Refractive Index Liquids were used as comparison solutions under a Leitz Metalloplan polarization microscope.

The X-ray opacity of the dental glasses was determined according to ISO 4049 (radio-opacity of dental composite materials) on solid samples of 1 mm thickness (instrument: Oralix DC from Gentix and evaluated with Prepress RP115 from Shamrock). As the reference for the measurement of the X-ray opacity, an aluminum standard spindle (Al 99.5%) of 1 to 5 mm thickness was used.

The chemical stability against NaF solution was determined by the following method:

For the qualitative corrosion test, 3 test pieces were needed. Two test pieces were tested in the NaF solution, and the third served as the reference sample. For the preparation of the test plates, the monomer mixture was taken, and the silanized glass filler (50 wt. %) was incorporated with a plastic spatula and homogenized by hand. The monomer-filler mixture was painted bubble-free into the steel test piece mold (round, diameter 15 mm, 1.5 mm thickness) and hot-cured. The curing of the monomer takes place under pressure, heat and in the water-bath (10 mins at 120° C. and 6 bar) in the Ivomat IP® 3 (Ivoclar Vivadent AG). Next, the test pieces were rough-ground with 1000 SiC paper and polished to high gloss on both sides with a 6 μm diamond suspension.

For the NaF test, two test pieces were boiled under reflux in 100 ml of 0.001% NaF solution for 16 hours. The assessment was performed qualitatively (visually) for color and transparency changes (comparison of the clouding with the reference sample) and by scanning electron micrography (SEM). In the SEM image, the occurrence of possible gaps between the filler particles and the surrounding monomer matrix was investigated. If the filler particles have not been chemically attacked by the acid test and are thus resistant, the embedding of the particles in the composite matrix remains intact. No cracks and gaps occur. The transparency of the composite test piece does not alter.

2. Practical Examples

The following table summarizes practical examples of the glasses according to the invention in terms of their compositions and most important properties.

Monomer Composition:

In order to be able to produce highly transparent composites with fillers in a refractive index range from 1.50 to 1.549, it is necessary to match the refractive index of the monomer mixture to the filler. This is possible on account of the very different refractive indices of TEGDMA and bis-GMA. The following table shows the refractive index of the monomer matrix as a function of the mixing ratio of TEGDMA and bis-GMA (values in wt. %).

| Bis-GMA | TEGDMA | Refractive index |
| --- | --- | --- |
| 85 | 15 | 1.5370 |
| 70 | 30 | 1.5233 |
| 41 | 59 | 1.4970 |
| 28 | 74 | 1.4849 |
| 10 | 90 | 1.4703 |

During the curing of the monomer matrix to a polymer, an increase in density takes place and hence an increase in the refractive index by ca. 0.025. As a result, the refractive index

| | Values in weight % | | | | | |
| --- | --- | --- | --- | --- | --- | --- |
| | 1 | 2 | 3 | 4 | 5 | 6 |
| $SiO_2$ | 58.00 | 58.00 | 54.00 | 58.00 | 63.00 | 58.00 |
| CaO | 2.00 | 2.00 | 9.00 | 2.00 | | |
| $Al_2O_3$ | 14.00 | 14.00 | 10.00 | 14.00 | 12.40 | 14.00 |
| MgO | 6.93 | 7.93 | 8.00 | 6.43 | 10.40 | 6.10 |
| $ZrO_2$ | 2.00 | 2.00 | | 2.00 | 3.90 | 0.40 |
| ZnO | 2.50 | 2.50 | 1.00 | | | |
| $La_2O_3$ | 9.57 | 1.57 | 7.00 | 1.57 | 8.20 | 1.50 |
| $WO_3$ | 2.00 | 10.00 | 5.00 | 10.00 | 2.00 | 10.00 |
| $B_2O_3$ | 3.00 | 2.00 | 6.00 | 6.00 | 0.10 | 10.00 |
| Total | 100.00 | 100.00 | 100.00 | 100.00 | 100.00 | 100.00 |
| Melting (° C./min) | 1650/75 1670/75 | 1800/80 1850/80 | 1650/90 | 1650/90 | 1650/75 1670/75 | 1650/90 |
| Color (glass) | light yellowish | light yellowish | colorless | colorless | light yellowish | colorless |
| Transparency | very good | very good | very good | good | good | good |
| Refr. index (Becke) | 1.546 | 1.534 | 1.548 | 1.528 | 1.548 | 1.512 |
| X-ray opacity (% Al) | 281 | 352 | 274 | 284 | 276 | 263 |
| Stability to NaF | very good | very good | very good | very good | very good | adequate, slight clouding |

3. Production Of A Filling Composite Based On X-Ray-Opaque Fillers

In accordance with the table presented below, a filling composite based on a methacrylate mixture with the inclusion of the X-ray-opaque fillers was produced by means of an LPM 0.1 laboratory kneader (Linden Co., Marienheide).

The milled fillers were first surface-treated with silane in accordance with the following formula (values in wt. %):

90% filler
9% γ-methacryl-oxypropyl-trimethoxy-silane
1% water

The components were placed together and homogenized in a Turbola mixer for 24 hours. The filler was then dried for a period of 4 days at 50° C.

range of the glasses which is claimed in the patent is covered by these monomer mixtures. Most monomers used in the dental industry are in a refractive index range from 1.47 to 1.53, so that the fillers according to the invention can also be used for other monomers.

The monomers are initiated with camphorquinone (0.25%), ethyl p-N,N-dimethylaminobenzoate (0.50%) and Lucirin® TPO (0.07%, BASF).

With the light-curing initiated monomer mixtures and the fillers according to the invention, composites were produced wherein the fillers were used at 70 wt. %. For the measurement of the X-ray opacity, the composite was irradiated twice for 3 mins with a Spectramat dental light source (Vivadent) and thus cured.

We claim:

1. A dental glass containing 50 to 70 wt. % of $SiO_2$,
   5 to 18 wt. % of $Al_2O_3$,
   6.1 to 30 wt. % of MgO,
   1 to 15 wt. % of $La_2O_3$,
   1 to 15 wt. % of $WO_3$,
   0.1 to 8 wt. % of $ZrO_2$,
   and optionally further oxides except for the oxides of Sr, Ba or alkali metals, wherein the stated quantities in total add up to 100 wt. %.

2. The dental glass as claimed in claim 1, wherein the sum of $La_2O_3+WO_3$ is 8 to 20 wt. %.

3. The dental glass as claimed in claim 1, wherein the sum of $Al_2O_3+La_2O_3+WO_3$ is 16 to 38 wt. %.

4. The dental glass as claimed in claim 1, wherein it contains
   50 to 70 wt. % of $SiO_2$,
   9 to 15 wt. % of $Al_2O_3$,
   6.1 to 30 wt. % of MgO,
   1 to 18 wt. % of $La_2O_3+Y_2O_3$,
   1 to 12 wt. % of $WO_3$, and
   0.1 to 8 wt. % of $ZrO_2$,
   wherein the sum of all components adds up to 100 wt. %.

5. The dental glass as claimed in claim 4, wherein the sum of $La_2O_3+Al_2O_3+Y_2O_3+ZrO_2$ is 16 to 38 wt. %.

6. The dental glass as claimed in claim 1, wherein it contains 8 to 20 wt. % of MgO.

7. The dental glass as claimed in claim 1, wherein it contains 0 to 15 wt. % of oxides of other divalent metals, except for Sr and Ba.

8. The dental glass as claimed in claim 7, wherein it contains CaO and ZnO.

9. The dental glass as claimed in claim 1, wherein it contains 0 to 20 wt. % of oxides of other trivalent and/or tetravalent metals.

10. The dental glass as claimed in claim 9, wherein it contains $B_2O_3$ and/or $TiO_2$.

11. The dental glass as claimed in claim 1, wherein it contains 0 to 4 wt. % of $Ag_2O$.

12. The dental glass as claimed in claim 1, wherein it contains from 0 to 2 wt. % of halides and/or sulfates.

13. A method for the production of dental glasses, wherein
   a) a glass melt is produced in the composition as claimed in claim 1,
   b) a glass frit is produced by cooling of the melt,
   c) the glass frit is pre-pulverized and
   d) a fine milling to powder is performed.

14. The method as claimed in claim 13, wherein the glass frit is produced by freezing of the melt.

15. The method as claimed in claim 13, wherein the pre-pulverization of the glass frit is effected to a size of 5 to 30 μm.

16. The method as claimed in claim 13, wherein the fine milling is effected by means of a wet milling.

17. The method as claimed in claim 16, wherein the fine milling is effected in a suspension with a solids content of 5 to 50 wt. %.

18. The method as claimed in claim 16, wherein the fine milling is effected to a particle size of 20 to 50 nm.

19. A dental composite comprising the dental glass as claimed in claim 1 as a glass filler.

* * * * *